United States Patent [19]

Straihammer et al.

[11] 4,278,429
[45] Jul. 14, 1981

[54] DENTAL HANDPIECE

[75] Inventors: Reinhard Straihammer, Einhausen; Werner Schuss, Heppenheim, both of Fed. Rep. of Germany

[73] Assignee: Siemens Aktiengesellschaft, Berlin & Munich, Fed. Rep. of Germany

[21] Appl. No.: 104,979

[22] Filed: Dec. 18, 1979

[30] Foreign Application Priority Data

Dec. 22, 1978 [DE] Fed. Rep. of Germany ....... 2855720

[51] Int. Cl.³ .............................................. A61C 1/08
[52] U.S. Cl. .................................. 433/126; 433/130; 433/105
[58] Field of Search ............... 433/105, 130, 126, 133, 433/146; 408/133; 74/416, 417, 332, 812

[56] References Cited

U.S. PATENT DOCUMENTS

| 219,849 | 9/1879 | Cushing | 433/130 |
|---|---|---|---|
| 374,286 | 12/1887 | Bell et al. | 433/130 |
| 600,243 | 3/1898 | Case et al. | 433/130 |
| 636,476 | 11/1899 | Webster | 433/130 |
| 647,010 | 4/1900 | Marshall | 433/130 |
| 3,229,369 | 1/1966 | Hoffmeister et al. | 433/105 |

FOREIGN PATENT DOCUMENTS

| 838938 | 5/1952 | Fed. Rep. of Germany | 433/130 |
|---|---|---|---|
| 890118 | 9/1953 | Fed. Rep. of Germany | 433/130 |
| 2535702 | 2/1976 | Fed. Rep. of Germany | 433/130 |

Primary Examiner—Gene Mancene
Assistant Examiner—John J. Wilson
Attorney, Agent, or Firm—Hill, Van Santen, Steadman, Chiara & Simpson

[57] ABSTRACT

A dental handpiece, which has a drive motor part connected to a housing and a head part with a socket for supporting a tool for rotation being releasably secured on the housing, characterized by the handpiece being convertible between an angled handpiece and a straight handpiece. This is accomplished by the housing being composed of a first housing member, a second housing member, a device for interconnecting the first and second housing members for swivel movement between a first position with their drive shaft sections extending at an angle to each other and a second position with the drive shaft sections being in axial alignment, and a device for holding the housing members in a selected one of the first and second positions. The head part has a sleeve of a configuration to telescopically cover the second housing member and the majority of first housing member while the members are held in one of the first and second positions so that by changing the head part to provide another head part having a sleeve with a different configuration, the handpiece is converted between an angled handpiece and a straight handpiece.

10 Claims, 8 Drawing Figures

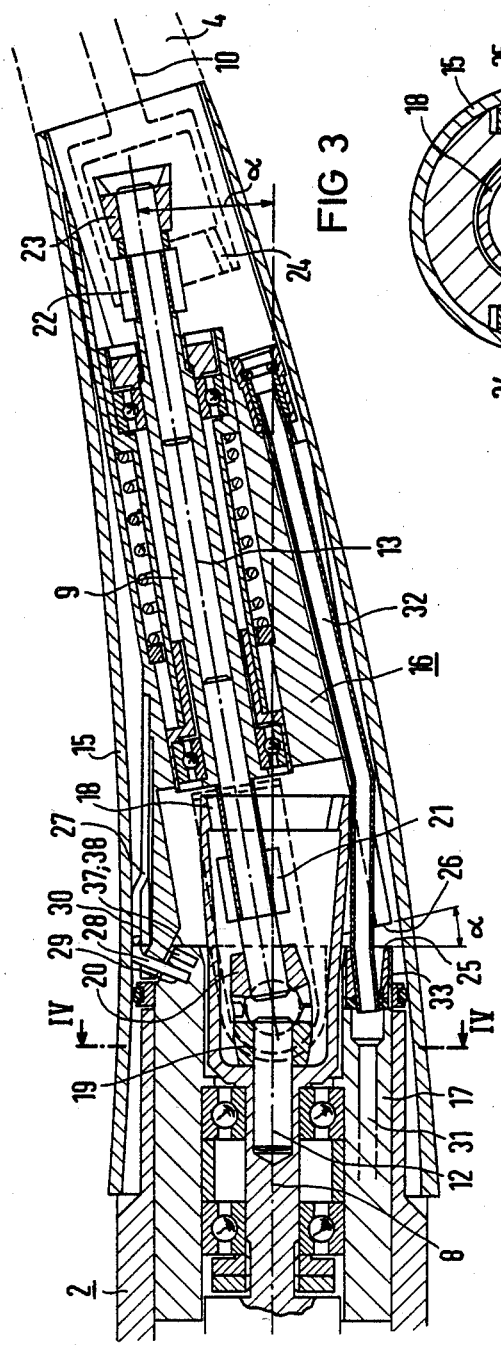
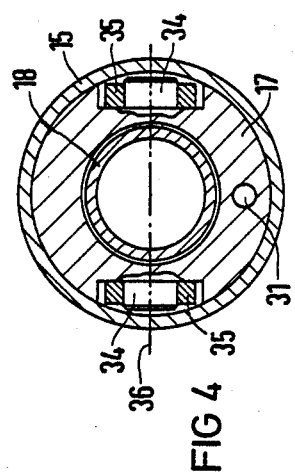
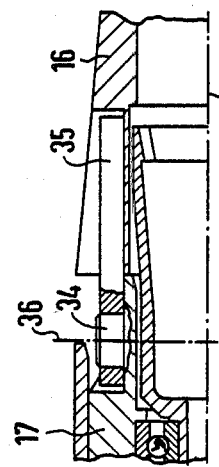
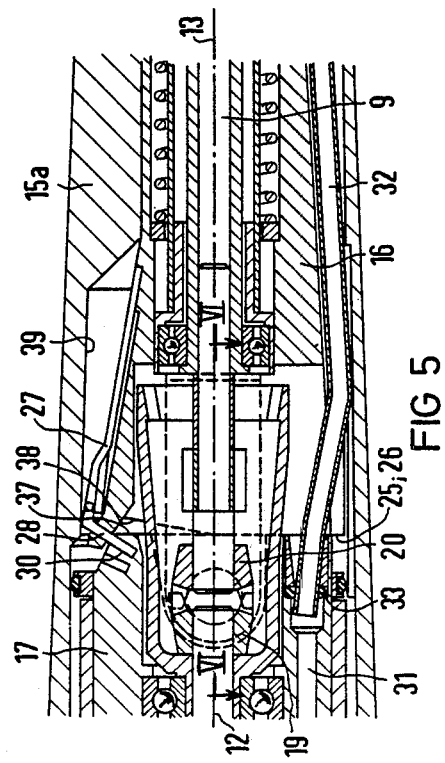

DENTAL HANDPIECE

BACKGROUND OF THE INVENTION

The present invention is directed to a dental handpiece which is convertible between an angled handpiece and a straight handpiece. The handpiece has a drive motor part with a drive motor, a housing containing a drive train with at least two drive shaft sections for transferring the rotary motion of the drive motor to a socket in the head part which socket mounts a tool for rotation.

In dental handpieces, one distinguishes between a so called straight handpiece and a so called angled handpiece. In a straight handpiece, the drive shaft sections of the drive train between the drive motor and the tool socket are arranged in axial alignment with each other or with the drive shaft sections being parallel to the axis to the drive shaft of the motor. In an angled handpiece, the drive shaft sections are arranged to be inclined to the drive axis of the motor adjacent the head part with an angle of approximately 18° to 21°. The dentist or physician will require both straight as well as angled handpieces for carrying out preparation work. Since angled handpieces, in particular, are also required with various transmission arrangements to enable a stepping-up in the speed of rotation and also a stepping-down in the speed of rotation, the provision of the desired number of handpiece parts or grip sections involves a relatively high investment for the dentist. If one takes into consideration that the various grip sections or handpiece parts must be frequently connected and disconnected from the drive motor part, these additional handpiece parts with their coupling and uncoupling will increase the wear of the various parts of the entire handpiece. In addition, since it is desirable at the present time to provide a cooling agent at the tool in the socket and for the handpiece to have the cooling lines extend through the drive motor part and grip section or handpiece part with appropriate coupling and sealing arrangement in the vicinity of the coupling of the drive motor part to the remaining handpiece part, the constant removal of the grip sections or handpiece parts from the drive motor will increase the wear of the coupling for the cooling lines with a corresponding increase in the chance of leaking of the cooling fluids.

SUMMARY OF THE INVENTION

The present invention is directed to providing a dental handpiece, which is an improvement in comparison to the presently known handpieces and has the goal of simplifying the use of both straight handpieces and angled handpieces with the corresponding reduction in the cost of the various handpieces. In addition, the present invention provides a dental handpiece that enables the use of both straight and angled handpieces with the reduction of wear of the coupling and sealed parts, which are present in the couplings of the cooling lines at the coupling of the drive motor part and the grip section or other handpiece parts.

To accomplish these objects, the present invention is directed to an improvement in a dental handpiece having a drive motor part with a drive motor, a handpiece housing connected to the drive motor part, a head part with a socket for supporting the tool for rotation being releasably secured on the housing, and drive train means received in the housing for transmitting rotary motion of the drive motor to the socket. The improvement comprises the handpiece housing being composed of a first housing member supporting a first drive shaft section and a second housing member supporting a second drive shaft section, each of said drive shaft sections being part of the drive train means and having gears disposed at their ends for engagement with adjacent drive shaft sections, means for interconnecting said first and second housing members for swivel movement between a first position with a drive shaft section having their gears in engagement and extending at an angle to each other and a second position with the drive shaft section having their gears in engagement and being axially aligned, means for selectively holding the housing members in a selected one of the first and second positions and said head part having a sleeve of a configuration to telescopically cover the second housing member and the majority of the first housing member while the members are held in one of said first and second positions so that by changing the head part with an other head part having a sleeve of a different configuration the handpiece can be converted between an angled handpiece and a straight handpiece.

A significant advantage of the invention solution is that parts of the handpiece such as the gear parts and the cooling agent lines sections with the associated coupling and sealing elements, which are relatively expensive from a standpoint of production technology need only be present once for both swivel positions which positions provide a straight handpiece for one of the two positions and an angled handpiece for the other position. Only an appropriate head part with either the angular gear or with a drive shaft section which is conducted straight through need be slipped onto the two sections with a sleeve covering the two housing members which are held in the appropriate swivel position for the particular sleeve configuration.

The two housing members may be interconnected by a trunnion type joint formed by trunnions extending from one of the two members which rotatably receive straps of the other member with a lock means comprising a groove disposed in one of the two members for each of the two positions and a resilient finger, which is formed on the end of a leaf spring, being received in the respective groove which depends upon the selected position and being held in the selected groove by the sleeve. In another embodiment, the means for forming the swivel connection include a portion of a ball surface of a ball and socket joint on a projection on one of the two members, a ring, which has a portion of a curved surface of the socket of a ball and socket joint engaged on the portion of the ball surface, being secured to the other of the two housing members and guiding pins which coact with grooves of the one member to hold the members in the selected one of the two positions. In this embodiment, the sleeve is again provided with an internal surface or contour which allows one of the pins to be in a retracted or disengaged position and the other to be in an engaged position so that the selected one of the two pins is controlled by the sleeve received on the housing members.

BRIEF DESCRIPTION OF THE DRAWINGS

FIG. 3 is a cross longitudinal cross section of a portion of the dental handpiece of FIG. 1;

FIG. 4 is a cross sectional view taken along the lines IV—IV of FIG. 3;

FIG. 5 is a partial longitudinal cross section of the dental handpiece when converted to a straight dental handpiece;

FIG. 6 is a partial cross section taken along the lines VI—VI of FIG. 5 with parts removed for purposes of illustration;

DESCRIPTION OF THE PREFERRED EMBODIMENTS

Figure 1:
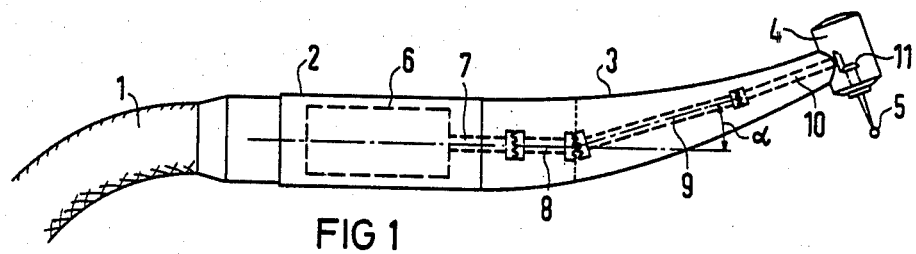
FIG. 1 is a schematic illustration of the dental handpiece in accordance with the present invention converted to an angled handpiece.
Figure 2:
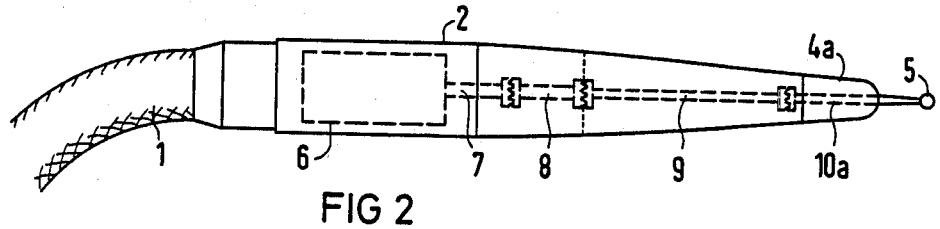
FIG. 2 is a schematic presentation of the dental handpiece in accordance with the present invention converted to a straight handpiece.

The principles of the present invention are particularly useful when incorporated in a dental handpiece which is schematically illustrated in FIG. 1 as it is arranged as an angled handpiece and converted to a straight handpiece as illustrated in FIG. 2. The dental handpiece, as illustrated in FIG. 1, has a drive motor part 2, which is attached to a supply hose 1, which will include cooling medium lines such as for water or air and conductors for supplying electric current to a drive motor 6 of the part 2. The drive motor part 2 is connected to an angled grip section or handpiece part 3 with a head part 4 that has a socket formed by a drive shaft section 11 for receiving and mounting a tool 5 for rotation. To transfer the rotary motion of a drive shaft of the motor 6 to the socket 11, the handpiece includes a drive train means including drive shaft sections 8, 9 and 10 which are provided with gears for meshing engagement. As illustrated, the drive shaft sections 8 and 9 are inclined to each other by an angle α. When the handpiece has been converted to a straight handpiece (FIG. 2), the head part is replaced by a head part 4a which has a drive shaft section 10a forming the socket for the tool 5. In this arrangement, the drive shaft section 9 and 8 are aligned with each other and also with the axis of the drive shaft 7.

In order to enable converting the handpiece from an angled handpiece as illustrated in FIG. 1 to the straight handpiece of FIG. 2, the housing, which supports the drive shaft sections such as 8 and 9 of the drive train, has a pair of housing members 16 and 17 with the member 17 supporting the shaft section 8 for rotation on an axis 12 and the member 16 supporting the shaft section 9 for rotation on an axis 13. The members 16 and 17 are interconnected by means, which enables swiveling between a first position with an axis 13 of the drive shaft 9, at an angle α to the axis 12 of the drive shaft 8 (FIG. 3), and a second position (FIG. 5) with the axes 12 and 13 being aligned. As illustrated, the housing section 17 is a component part of the housing of the drive motor part 2 and contains the drive shaft 8, which has two driving gears 18 and 19. The gears 18 and 19 are axially spaced apart along the axis 12 and as illustrated the gear 19 is a crown gear that is engaged with a crown gear 20 of the drive shaft section 9 which also has a driving gear 21 axially spaced from the gear 20. At the other end, the drive shaft section 9 has a pair of gears 22 and 23 which are spaced part and as illustrated the gear 22 is engaged with a gear 24 of the drive shaft 10 of the head part 4.

The drive shaft section 9 is mounted to be axially displaced in the member 16 between a position illustrated with the crown gears 20 and 19 in engagement to a position with the gears 20 and 19 out of engagement and the gear 21 in engagement with the gear 18. In the position illustrated, the gears 19 and 20 provide a direct drive with a 1:1 ratio between the shafts 8 and 9 and the gear 22 engaged with a gear 24 of the shaft section 10 provides a step-down ratio. If the head part 4 is changed to another head part, which does not have a sleeve portion extending in the housing as far as the head part 4, the shaft 9 will shift to the other position with the gear 21 engaged with the gear 18 and the crown gear 23 will engage with another similar crown type gear so that a step-up rotation will occur. A more detailed description of the displaceable drive shaft section is contained in U.S. patent application Ser. No. 100,000 filed Dec. 4, 1979, which is based on German Pat. application No. P 28 55 797.3 and reference with regard to the operation of the displaceable drive shaft section is made thereto.

The two housing members 16 and 17 have contact surfaces 25 and 26 (FIG. 3) and 37 and 38 (FIG. 5) on their ends. As illustrated, the surfaces 37 and 25, which are formed on the end of the member 17, lie substantially in the same plane while the surfaces 26 and 38 of the member 16 lie in two planes, which extend at an angle α to each other. These contact surfaces control the angle between the axes 12 and 13. Thus surfaces 37 and 38, when engaged (see FIG. 3), set the axis 12 at an angle α to the axis 13. When surfaces 25 and 26 are engaged (see FIG. 5), the axes 12 and 13 are aligned and extend in a straight line.

To hold the members 16 and 17 in the first position (FIG. 3) and the second position (FIG. 5), one of the members such as the member 17 is provided with grooves or depressions 29 and 30. The other member 16 has a leaf spring fastener 27, which has a bent end, which forms a stop finger 28, which will be engaged in the groove 29, when the spring 27 is forced into an engaged position by contact with the inner surface or contour of a sleeve 15 attached to the head part 4 to lock the members 16 and 17 in the first position. When a sleeve 15a, which is attached to a head part such as 4a, is provided, the finger 28 will be forced into engagement into the groove 30 (FIG. 5) to lock the members 16 and 17 in the second position.

To provide a cooling fluid in the vicinity of the tool 5, cooling lines formed by cooling line segments such as 31 in members 17 and 32 secured to member 16 are provided. As illustrated, to form a flexible coupling therebetween, a plug type connection 33 is provided and is formed by a socket formed in the housing 17 and provided with an elastic O-ring to receive an end of the line 32, which is inserted therein. It should be noted that the line 32 is provided with an unnumbered plug-in socket of a similar construction for receiving an end of a cooling line segment of the head part. It is also noted that during movement between the first and second position, such as illustrated in FIGS. 2, 3 and 5, the connection 33 compensates for any of the angular rotation and maintains the coupling.

To provide the swivel connection, the device of FIGS. 3, 4, 5 and 6 has a pair of pegs or trunnions 34,34 which are diametrically arranged on the housing member 17 on an axis 36 (FIG. 6). The member 16 has a pair of narrow bearing bands or straps 35 which have apertures for receiving the pegs 34 and are fixedly secured in the member 16. Thus, the housing member 16 can be swiveled around the axis 36 by an angle α with the amount of movement between the two positions being controlled by the contact surfaces so that the position illustrated in FIG. 3 is determined by engagement of the contact surfaces 37 and 38 and the position of FIG. 5 being determined by the contact surfaces 25 and 26.

To obtain the first position, the member 16 is moved to the position with the contact surfaces 37 and 38 engaged and then the head part 4 with the sleeve 15 is inserted on to the housing members to telescopically receive the housing member 16 and a part of the housing member 17. As illustrated, a housing member 17 is provided with a ring having an O-ring seal to form a seal between the interior of the sleeve 15 and member 17, and the head part and sleeve can be held in the housing by a known connection means. As the sleeve 15 is inserted, its inner surface or contour engages the spring 27 to force the finger 28 into the groove 29 to lock the members in the first position. It is also noted that while in this position, the gears 19 and 20 will be in exact meshing relationship and if the shaft section 9 is displaced along the axis 13, the gear 21 will mesh with the gear 18.

If the sleeve 15 with the head part 4 is actually removed from the two housing members 16 and 17, the stop finger 28 will then snap out of the groove 29 of the housing section member 17 to unlock or release the position of the members. The housing member 16 can now be rotated or pivoted around the axis 36 to the second position, which is determined by the contact surfaces 25 and 26. While in the second position, a straight handpiece can now be formed by providing a head part such as 4a (FIG. 2) which has a straight sleeve 15a, which is slipped on the housing member 16 and has appropriate guiding surface 39 on the interior of the sleeve to engage the spring 27 to force the finger 28 into the groove 30. In this position, the handpiece is now locked in the straight position in which the drive shaft axes 12 and 13 are aligned with one another. In this position, the two drive pinions 19 and 20 are also precisely engaged so that all of the teeth are meshing with each other. However, it should be noted that if the shaft section 9 is displaced to the right, the gears 21 will not engage with the gear 18.

Figure 8:
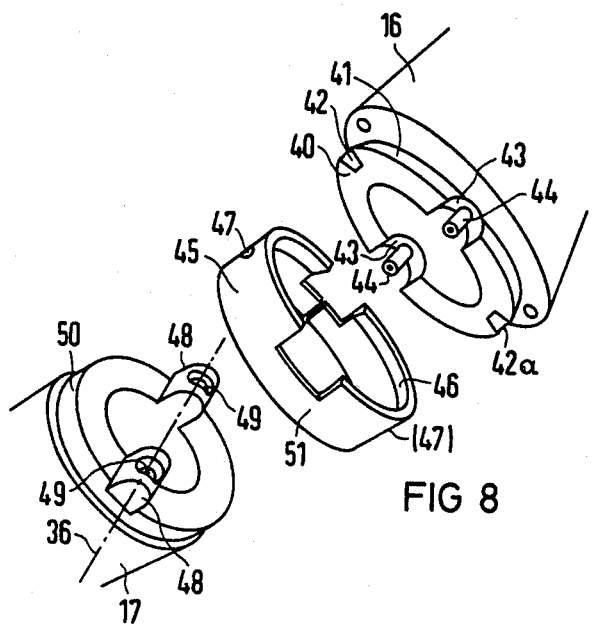
FIG. 8 is an exploded isometric of the parts of the swivel connection of FIG. 7.
Figure 7:
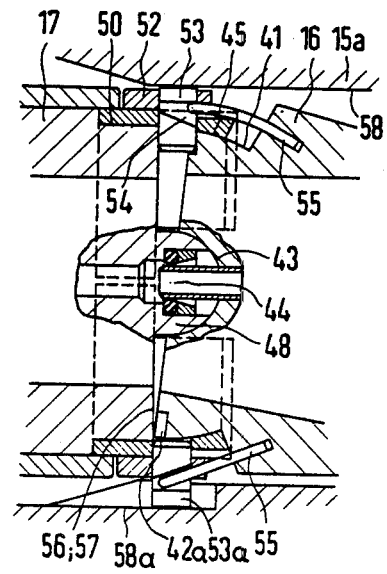
FIG. 7 is a second embodiment of a swivel connection in accordance with the present invention.

An embodiment of the means for interconnecting the housing members 16a and 17a is illustrated in FIGS. 7 and 8. In this embodiment, the housing section 16a has a projection 40 which has a spherical curved surface 41, which forms a portion of the surface of a ball of a ball and socket joint and has two radial recesses or grooves 42 and 42a which extend diametrically from each other. In addition, the projection 40 has a pair of recesses 43, which lie on a line extending perpendicular to the line formed by the grooves 42,42a and each recess 43 is provided with a projecting cooling line tube 44.

A resilient supporting ring 45, which is provided with a slot, has an internal curved surface 46, which is a portion of a spherical socket of a ball and socket joint and the surface 46 conforms to the curved surface 41. The ring 45 is received on a circular axial projection 50 of the member 17a, which also has two projections 48, which are received in the recesses 43 and coact therewith to form counter seats. Each of the projections 48 is provided with a bore or hole 49, that receives an elastic O-ring to form a plug-in type connection to receive the end 44 of the cooling line in the corresponding recess 43 of the member 16a. The ring 45 is also provided with a pair of holes 47 so that when the ring is received on the collar 50 of the member 17a, pins 53,53a which are mounted in the holes 47 are free to move radially into and out of engagement with the grooves 42, and 42a of the projection 40. As illustrated, the ring 45 may be provided with cut out portions adjacent the side portion 51 which are alinged with the projections 48.

In assembly, the surface 46 of the ring 45 is secured on the curved surface 41 (FIG. 7). Then the sections 51 are slipped behind the projections 48 so that the remaining surface of the ring is engaged on the collar 50. Pins 53,53a are now introduced into the holes 47 and into the respective grooves such as 42 by a second ring 52, which allows the pins 53 and 53a to be moved radially between an engaged position such as illustrated by the top pin 53 in FIG. 7 to a disengaged or retracted position illustrated by the bottom pin 53a. Each of the pins 53,53a has a lateral recess 54 which receives a spring element or spring wire 55 that is secured in the housing member 16a. The spring wire urges its pin to the outer, retracted position, which is the position of the pin 53a of FIG. 7. However, in the position illustrated in FIG. 7, the end surfaces 56 and 57 of the members 17a and 16a are engaged adjacent the pin 53a so that the axis of the two housing portions lie aligned. Thus, the top pin 53 will be urged into the groove 42 by an inner contour or surface 58 of the sleeve 15a to prevent pivoting of the housing members 16a and 17a to the first position with the housing members at an angle to each other. In order to better compensate for manufacturing tolerances and to adjust the axial play of the two housing members, the ring 45 is advantageously screwed onto the part 17a.

The sleeve 15a, which forms a straight handpiece together with the head part 4a, has the internal configuration 58, which is formed by the inner surface which had a recess 58a that allowed the pin 53a to remain in the retracted or radially outward position. If the sleeve 15a is pulled off of the two housing sections 16a and 17a, then the spring wires 55 will press both pins 53,53a radially to the retracted position. When the pins 53 and 53a are both in the retracted position, the housing member 16a can be rotated or pivoted relative to the member 17a on a pivot axis 36, which is formed by the projections 48 engaged in the recesses 43. If the housing section 16a is rotated until its end surfaces adjacent the pin 53 engaged the end surfaces of the member 17a and the axes 12 and 13 are at an angle α with respect to one another, then the upper pin 52 will engage the outer curve surface 41 while the lower pin 53a will be aligned to fall into or be engaged in the groove 42a. By inserting the headpiece part and sleeve for an angled handpiece onto the members while they are in this position, the pin 53a will be forced against the spring 55 into the groove 42a to lock the members in the angled position. The sleeve for the angled handpiece will be similar to the sleeve 15a except that a recess which is similar to the recess 58a will be provided adjacent the pin 53 to enable it to remain in the outer, retracted position.

A significant advantage of the handpiece of the present invention, is that both a straight as well as an angled shaped handpiece design can be realized by utilizing the same drive section, cooling line sections and sealing elements. Accordingly, dentists need only a single basic handpiece part having the housing portion 16 and 17 or 16a and 17a and need only slip on a corresponding head part with a sleeve which has either the configuration for a straight handpiece or an angled handpiece.

An advantageous design has the drive shaft seftion 8 together with the housing section 17 formed as a component part of the housing of the drive motor part 2. Thus, a greater selection of angled handpieces and straight handpieces with the angled handpieces being able to have either direct drive rotation, a stepped-up rotation or a stepped-down rotation can be accomplished with a minimum number of drive train elements. Thus the handpiece can be produced with a greater savings.

Although various minor modifications may be suggested by those versed in the art, it should be understood that we wish to employ within the scope of the patent granted hereon, all such modifications as reasonably and properly come within the scope of our contribution to the art.

We claim:

1. In a dental handpiece having a drive motor part with a drive motor, a handpiece housing connected to the drive motor part, a head part with a socket for supporting a tool for rotation being releasably secured on the housing and drive train means received in the housing for transmitting rotary motion of the drive motor to said socket, the improvement comprising the handpiece housing being composed of a first housing member supporting a first drive shaft section and a second housing member supporting a second drive shaft section, each of said drive shaft sections being part of the drive train means and having gears disposed at their ends for engagement with adjacent drive shaft sections, means for interconnecting said first and second housing members for swivel movement between a first position with the first and second drive shaft sections having their gears in engagement and extending at an angle to each other and a second position with the first and second drive shaft sections having their gears in engagement and being axially aligned, means for selectively holding said housing members in a selected one of the first and second positions, and said head part having a sleeve of a configuration to telescopically cover the second housing member and the majority of the first housing member while the members are held in one of said first and second positions, said sleeve having and interior engaging a portion of the means for holding to activate said means for holding so that by changing the head part with another head part having a sleeve with a different configuration, said handpiece can be converted between an angled handpiece and a straight handpiece.

2. In a dental handpiece accordig to claim 1, wherein the means for holding said housing members includes lock means for locking the housing members in the selected one of the first and second positions, said lock means being provided on one of said housing members and sleeve.

3. In a dental handpiece according to claim 2, wherein the lock means is disposed on one of said housing members, the inner contour of the sleeve being arranged to receive the pair of the first and second housing members while only in one of said first and second positions, said inner contour engaging said lock means during assembly to cause locking of the members in the selected position.

4. In a dental handpiece according to claim 1, wherein each of said housing members adjacent the means for connecting having an end surface engaging an end surface of the other housing member, one of said end surfaces being planar and the other end surface being formed by two plane portions extending at the angle of inclination to each other so that the angle of the first position and the axial alignment of the second position are controlled by engagement of the end surfaces.

5. In a dental handpiece according to claim 1, wherein the means for interconnecting includes one of said housing members being provided with a pair of trunnions, the other of said housing members having a pair of straps rotatably received on said trunnion and said holding means including one of said first and second members having first and second grooves associated with said first and second position respectively and a spring loaded finger being mounted on the other of said housing members and engageable in one of said first and second grooves as the members assume the first and second positions, respectively.

6. In a dental handpiece according to claim 5, wherein the finger is an end of a leaf spring mounted on the other housing member, said finger being held in engagement in its respective groove by contact with the inner contour of the sleeve attached to the head part.

7. In a dental handpiece having a drive motor part with a drive motor, a handpiece housing connected to the drive motor part, a head part with a socket for supporting a tool for rotation being releasably secured on the housing and drive train means received in the housing for transmitting rotary motion of the drive motor to said socket, the improvement comprising the handpiece housing being composed of a first housing member supporting a first drive shaft section and a second housing member supporting a second drive shaft section, each of said drive shaft sections being part of the drive train means and having gears disposed at their ends for engagement with adjacent drive shaft sections, means for interconnecting said first and second housing members for swivel movement between a first position with the first and second drive shaft sections having their gears in engagement and extending at an angle to each other and a second position with the first and second drive shaft sections having their gears in engagement and being axially aligned, said means for interconnecting including one of the housing members having a projection with a portion of a spherical ball surface of a ball and socket joint, a support ring having a curved surface of a socket for said ball and socket joint engaged on the ball surface, said support ring being connectable to the other housing member, means for selectively holding said housing members in a selected one of the first and second positions, said means for selectively holding including a pair of diametrically opposed pins provided on said ring, a pair of grooves formed in the one housing member for receiving said pair of pins, so that one of said pair of pins locks the member in said first position and other pin of the pair while in the other of said pair of grooves locks the members in said second position, and said head part having a sleeve of a configuration to telescopically cover the second housing member and the majority of the first housing member while the members are held in one of said first and second positions so that by changing the head part with another head part having a sleeve with a different configuration, said handpiece can be converted between an angled handpiece and a straight handpiece.

8. In a dental handpiece according to claim 7, wherein said pins are received in a radially extending holes and urged radially outward by means of a spring and into engagement with the respective groove by an inner surface of said sleeve.

9. In a dental handpiece according to claim 8, wherein each sleeve contains a guidance surface for one of said pins, said guidance surface urging said one pin radially inward to lock the members in one of said positions and allowing the other pin to be in an outer retracted position.

10. In a dental handpiece according to claim 7, wherein the holding means include a pair of diametrically opposite projections extending from one member in a plane extending 90° to the plane of said pins, the other of said members having a pair of recesses for receiving said projections, one of each recess and projection having a socket communicating with a cooling line and having an elastic sealing element for receiving a cooling line projecting from the other of said recess and projection to form a plug-in connection between the two cooling lines.

* * * * *